US 7,894,651 B2

(12) United States Patent
Gutkowicz-Krusin et al.

(10) Patent No.: US 7,894,651 B2
(45) Date of Patent: Feb. 22, 2011

(54) QUANTITATIVE ANALYSIS OF SKIN CHARACTERISTICS

(75) Inventors: Dina Gutkowicz-Krusin, Princeton, NJ (US); Joseph V. Gulfo, New York, NY (US)

(73) Assignee: MELA Sciences, Inc., Irvington, NY (US)

( * ) Notice: Subject to any disclaimer, the term of this patent is extended or adjusted under 35 U.S.C. 154(b) by 998 days.

(21) Appl. No.: 11/681,345

(22) Filed: Mar. 2, 2007

(65) Prior Publication Data
US 2008/0214907 A1 Sep. 4, 2008

(51) Int. Cl.
*G06K 9/00* (2006.01)
(52) U.S. Cl. .......................... 382/128; 606/9
(58) Field of Classification Search .......... None
See application file for complete search history.

(56) References Cited

U.S. PATENT DOCUMENTS

| | | | | |
|---|---|---|---|---|
| 6,208,749 | B1 * | 3/2001 | Gutkowicz-Krusin et al. | 382/128 |
| 6,215,893 | B1 | 4/2001 | Leshem et al. | |
| 6,648,820 | B1 | 11/2003 | Sarel | |
| 6,770,029 | B2 * | 8/2004 | Iliff | 600/300 |
| 6,792,137 | B2 | 9/2004 | Kenet | |
| 7,162,063 | B1 * | 1/2007 | Craine et al. | 382/128 |
| 7,647,285 | B2 * | 1/2010 | Heckerman et al. | 706/20 |
| 2005/0171439 | A1 | 8/2005 | Maschke | |
| 2005/0251415 | A1 * | 11/2005 | Pak | 705/2 |
| 2006/0269111 | A1 * | 11/2006 | Stoecker et al. | 382/128 |
| 2008/0049990 | A1 * | 2/2008 | Melchi et al. | 382/128 |
| 2008/0214907 | A1 * | 9/2008 | Gutkowicz-Krusin et al. | 600/306 |

OTHER PUBLICATIONS

Dermlite: http://www.dermlite.com/fotosyspro.html, DemiLite FOTO + DermLite FOTOsystem, pp. 1-6, Mar. 6, 2007.
International Search Report, Patent Cooperation Treaty, dated Jun. 25, 2008 (10 pages).
"Poster Abstracts," *Supplement to the Journal of the American Academy of Dermatology*, 54(3) (Mar. 2006), American Academy of Dermatology 64th Annual Meeting, Mar. 3-7, 2006.
Abbasi, N. R., et al. "Early diagnosis of cutaneous melanoma. Revisiting the ABCD criteria." *JAMA*; 292:2771-2776 (2004).
Bono, A., et al. "The ABCD system of melanoma detection." *Cancer*, 85:72-77 (1999).
Elbaum, M., et al. "Automatic differentiation of melanoma from melanocytic nevi with multispectral digital dermoscopy: a feasibility study." *J Am Acad Dermatol*, 44:207-218 (2001).

(Continued)

*Primary Examiner*—Andrew W Johns
*Assistant Examiner*—Tahmina Ansari
(74) *Attorney, Agent, or Firm*—Fish & Richardson P.C.

(57) ABSTRACT

Skin characteristics are analyzed. A device acquires a digital image of an area of skin of a user. A processor quantitatively analyzes the digital image to determine a characteristic of all or part of the area of skin which is indicative of a skin condition of interest. Depending on the results of the quantitative analysis, the processor provides information to the user about the area of skin relative to the condition of interest. The information provided to the user is not necessarily sufficient for a definitive medical diagnosis and may include an indication to the user as to whether a knowledgeable person should evaluate the area of skin.

40 Claims, 5 Drawing Sheets

OTHER PUBLICATIONS

Figure 1A:
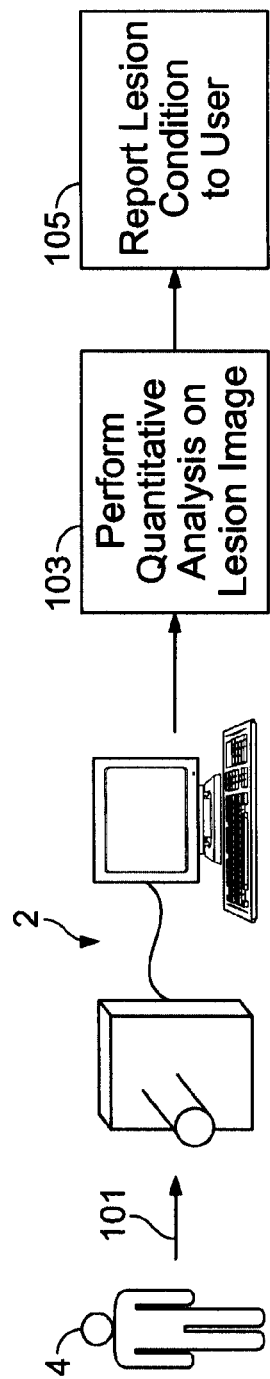

Friedman, R. J., et al. "Early detection of malignant melanoma: the role of physician examination and self-examination of the skin." *CA Cancer J Clin*, 35:130-151 (1985).

Gutkowicz-Krusin, D., et al. "Precision of automatic measurement of parameters of pigmented skin lesions with a multispectral digital dermoscope MelaFind." *Melanoma Res*, 10:563-570 (2000).

Kopf, A. W., et al. "Atypical mole syndrome." *JAAD*, 22:117-118 (1990).

Schaefer, T., et al. "The epidemiology of nevi and signs of skin aging in the adult general population." *J Invest Dermatol*, 126:1490-1496 (2006).

Thomas, L., et al. "Semiological value of ABCDE criteria in the diagnosis of cutaneous pigmented tumors." *Dermatology*, 197:11-17 (1998).

Tsao, H., et al. "The transformation rate of moles (melanocytic nevi) into cutaneous melanoma." *Arch Dermatol*, 139:282-288 (2003).

Gutkowicz-Krusin, D., et al. "Evaluation of clinical and quantitative ABCD characteristics of pigmented skin lesions in the diagnosis of melanoma." Presented at the American Academy of Dermatology Annual Meeting, San Francisco, CA. Mar. 3, 2006 (abstract).

DermoGenius Basic II brochure, pp. 1-5.

DermoGenius http://www.dermogenius.com/index.php?id=72 &L=1, DermoGenius Ultra, pp. 1-2, Mar. 2, 2007.

DermoGenius http://wwwdermogenius.com/DermoGenius-basic-II. 68.0html&L=1, DermoGenius Basic II, p. 1, Mar. 2, 2007.

DermoGenius http://www.dermogenious.com/DermoGenius-lite. 70.0.html?&L=1, DermoGenius Lite, pp. 1-2, Mar. 2, 2007.

DermoGenius http://www.dermogenius.com/DermoGenius-MoleMap.78.0.html?&L=1, DermoGenious + MoleMap, p. 1, Mar. 2, 2007.

SolarScan: http://www.polartechnics.com.au/proSolar.htm Mar. 2, 2007.

SolarScan: http://www.polartechnics.com.au/SolarTech.htm, pp. 1-3, Mar. 2, 2007.

Siascope: http://www.astronclinica.com/technology/siascopy-explained.htm, What is SIAscopy?, Mar. 2, 2007, pp. 1-4.

Siascope: http://www.astronclinica.com/products/contact-siascopy. htm, SIAscope V—Contact SIAscopy, Mar. 2, 2007, pp. 1-3.

Siascope: http://www.astronclinica.com/products/non-contact-siascopy.htm, Digital Camera—Non-Contact SIAscopy, Mar. 2, 2007, pp. 1-2.

Siascope: http://www.astronclinica.com/products/molemate.htm, MoleMate, Mar, 2, 2007, pp. 1-5.

Siascope: http://www.astronclinica.com/products/moleview.htm, MoleView, Mar. 2, 2007, pp. 1-4.

Siascope: http://www.astronclinica.com/products/molemanager. htm, MoleManager, Mar. 2, 2007, pp. 1-3.

Siascope: http://www.astronclinica.com/products/basal-cell-carcinoma.htm, BCC View, Mar. 2, 2007, pp. 1-3.

DermoGenius http://www.dermogenius.com/DermoGenius-MoldMap.78.0.html?&L=1, DermoGenius + MoleMap, p. 1, Mar. 2, 2007.

Siascope: http://vvww.astronclinica.com/products/moleview.htm, MoleView, Mar. 2, 2007, pp. 1-4.

* cited by examiner

20d

23

25

The Above Region of Skin Requires Further Evaluation by a Medical Professional.

Would you Like to Schedule an Appointment with your Physician? Y/N

20d

23

25

The Above Region of Skin is Unlikely to be Melanoma.

\* However, Lesions or Areas of Skin with Changing Features should be Evaluated by a Medical Professional.

QUANTITATIVE ANALYSIS OF SKIN CHARACTERISTICS

BACKGROUND

This disclosure relates to quantitative analysis of skin characteristics.

Skin lesions, for example, include tissue on or in the skin that has abnormal characteristics. In general, skin lesions are malignant, pre-malignant or benign and also can be categorized based on physical characteristics. Some skin lesions are pigmented and others are non-pigmented. Examples of pigmented malignant and pre-malignant lesions include melanoma, some basal cell and squamous cell carcinomas and actinic keratoses. Examples of pigmented benign lesions include low-grade dysplastic nevi, congenital nevi and seborrheic keratoses.

Dermatologists or other physicians determine whether a particular lesion on a patient's skin should be biopsied to rule out melanoma. The determination is especially difficult for early stage melanoma lesions which are similar to many benign pigmented lesions. Analysis by a dermatologist of malignant and benign lesions entails subjective visual assessment of lesion characteristics.

SUMMARY

In one aspect, an apparatus for analyzing skin characteristics includes a device to acquire a digital image of an area of skin and a processor to quantitatively analyze the digital image. The processor determines a characteristic of all or part of the area of skin that is indicative of a skin condition of interest and, depending on results of the quantitative analysis, provides information to a user about the area of skin relative to the condition of interest. The information includes an indication to the user as to whether a knowledgeable person should evaluate the area of skin.

Implementations may include one or more of the following features. For example, the information may include a classification of the skin condition of interest. The information may not be necessarily sufficient for a definitive medical diagnosis.

The quantitative analysis may include comparing the characteristic of all or part of the area of skin to a threshold associated with the condition of interest.

The characteristic indicative of a skin condition of interest may have a high specificity and high sensitivity in a general population. Both the specificity and sensitivity may be greater than 90 percent in the general population. The characteristic that is indicative of a skin condition of interest may not be recognizable by visual inspection by a physician.

Part of the area of skin may include a pigmented skin lesion. The condition of interest may include malignancy. The quantitative analysis may suggest that malignancy can or cannot be ruled out.

The processor may provide an indication to a user that it is not necessary to have the area of skin evaluated by a knowledgeable person. The processor may provide an indication that it is advisable to have the area of skin evaluated by a knowledgeable person. The user may not be a licensed health care provider or a physician. The knowledgeable person may be a physician and the user may be someone other than a physician. The knowledgeable person may be a dermatologist and the user may be a physician other than a dermatologist.

The apparatus may include an audible or visible indicator that provides the information about the area of skin relative to the condition of interest.

The device may acquire, at different times, digital images of the area of skin and quantitatively analyze the different digital images. The processor may compare the results of the quantitative analysis for each image and, based on the comparison, indicate whether a change in a condition of the area of skin has occurred.

The device may be configured to be applied to the skin. The device may be triggered by the user to acquire the digital image. At least part of the apparatus may be handheld.

In another aspect, a quantitative analysis is performed on an image of an area of skin to determine a characteristic of all or part of the area of skin that is indicative of a condition of interest. Information may be provided to a user about the area of skin relative to the condition of interest, based on the quantitative analysis. The information includes an indication to the user whether a knowledgeable person should evaluate the area of skin.

The information may not be necessarily sufficient for a definitive medical diagnosis.

Images of the area of skin may be acquired at different times and a quantitative analysis on each of the images may be performed to determine, for each image, a characteristic of all or part of the area of skin. The results of the quantitative analysis may be compared for each image. Information may be provided to the user, based on the comparison, that indicates whether a change in condition of the area of skin has occurred.

The knowledgeable person may be a physician and the user may be someone other than a physician. The knowledgeable person may be dermatologist and the user may be a physician other than a dermatologist.

In another aspect, a person's skin is quantitatively determined whether it is characterized by a condition of interest, based on an image of the person's skin and statistical information about skin of people in a general population. The quality of the determination is sufficient to reliably indicate whether examination by an expert of the skin relative to the condition of interest is desirable.

In another aspect, an image of a region of skin of a person is automatically analyzed and an indication that a condition of the region of skin should be analyzed further by a human expert is automatically provided.

In another aspect, qABCD parameter values of images of skin lesions are quantitatively determined. Based on statistical information from a general population, lesions that are non-melanoma and lesions that cannot be ruled out as melanoma are determined with a high sensitivity and specificity. An indication of the result of the determination, which is based on statistical information, is provided.

In another aspect, qRING parameter values of images of skin lesions are quantitatively determined. Based on statistical information from a general population of humans, lesions that are non-melanoma and lesions that cannot be ruled out as melanoma are determined with a high sensitivity and specificity. An indication of the result of the determination, which is based on statistical information, is provided.

Implementations may include one or more of the following features. Each qABCD parameter value may be compared to a corresponding threshold value. A qABCD characteristic may be determined as present if the corresponding qABCD parameter value is greater than the corresponding threshold value. A qABCD characteristic may be determined as absent if each qABCD parameter value is less than the corresponding threshold value.

Each qRING parameter value may be compared to a corresponding threshold value. A qRING characteristic may be determined as present if the corresponding qRING parameter value is greater than the corresponding threshold value. A qRING characteristic may be determined as absent if each qRING parameter value is less than the corresponding threshold value.

Each threshold value may be derived from a reference database of imaged skin lesions in which each threshold value maximizes a diagnostic accuracy of a corresponding qABCD or qRING parameter value. An indication of the advisability of having the skin lesions evaluated by a knowledgeable person may be provided if one or more qABCD characteristics or qRING characteristics is present. The sensitivity and specificity of the qABCD characteristics and qRING characteristics may be greater than 90 percent.

In another aspect, an apparatus includes a camera for acquiring a digital image of a region of skin that has a skin lesion. A processor connected to the camera is programmed to quantitatively analyze the digital image to determine the presence of a characteristic, indicative of malignancy, in the skin lesion. The processor may provide an indication to a user to have the skin lesion evaluated by a knowledgeable person if the characteristic is present. The processor may provide an indication to the user that it is not necessary to have the skin lesion evaluated by a knowledgeable person if the characteristic is not present. The apparatus also includes a display for viewing the skin lesion image and indication provided by the processor.

Other features and advantages will be apparent from the description and from the claims.

DESCRIPTION

Figure 1B:
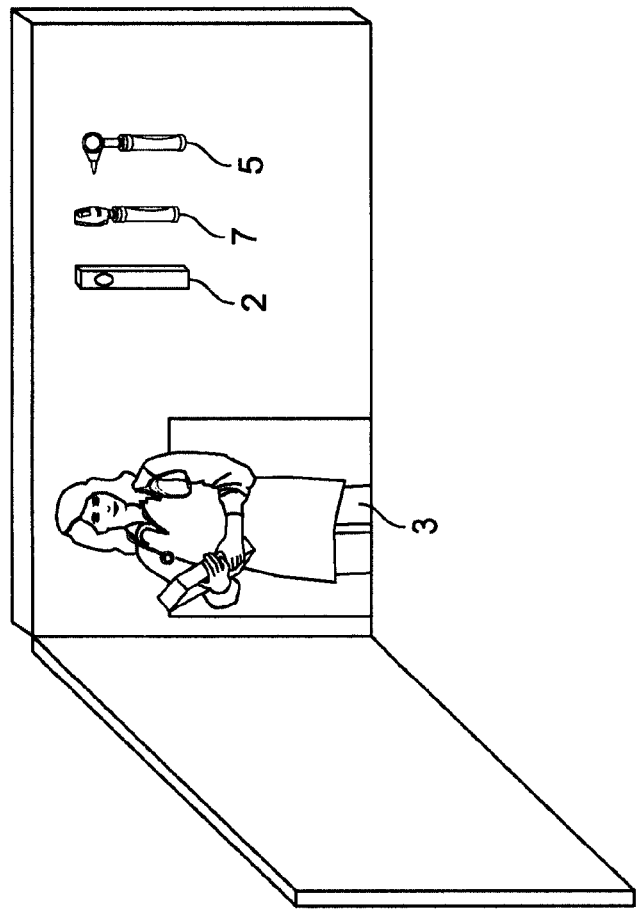
Figure 2:
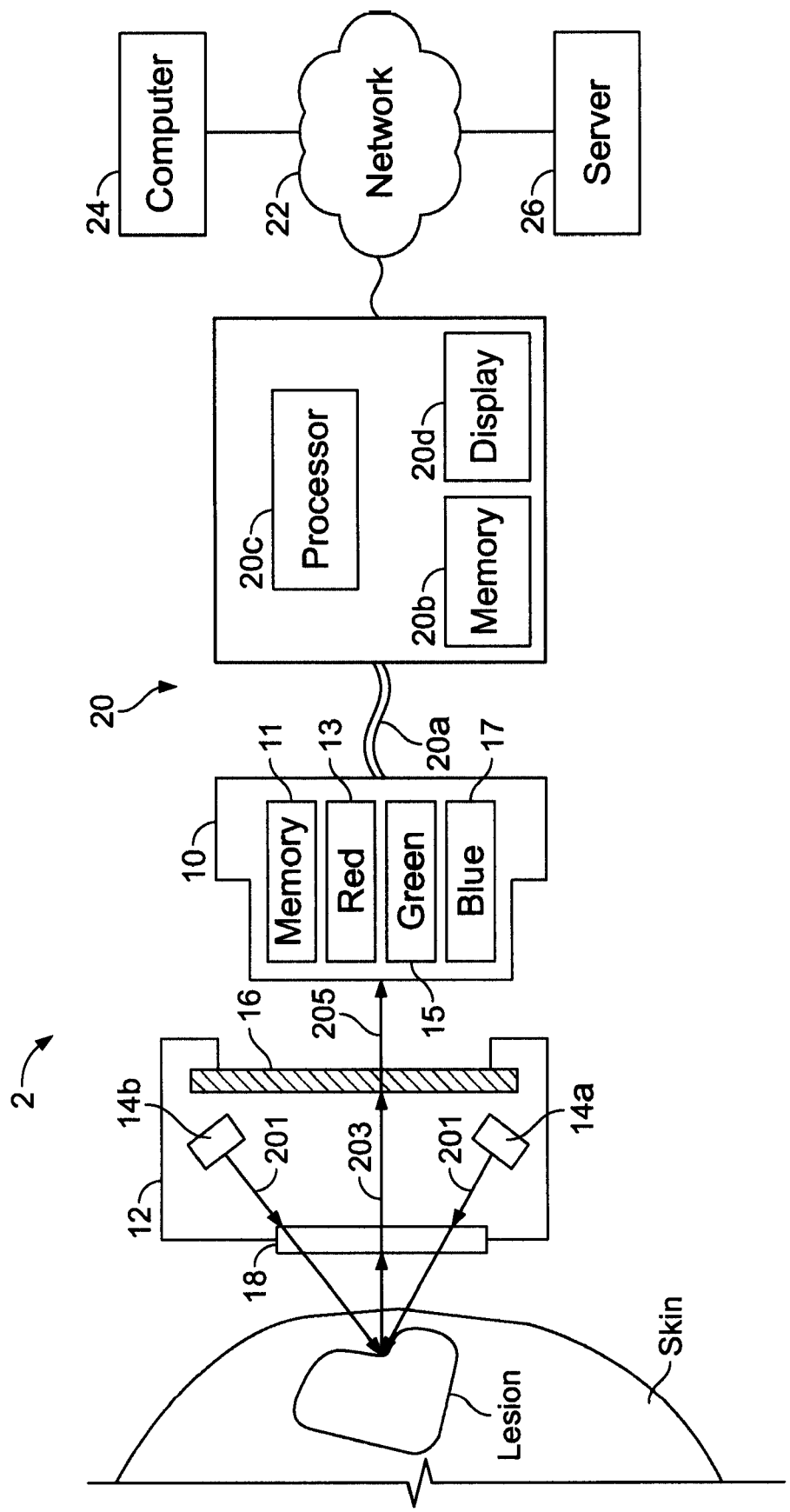
Figure 3A:
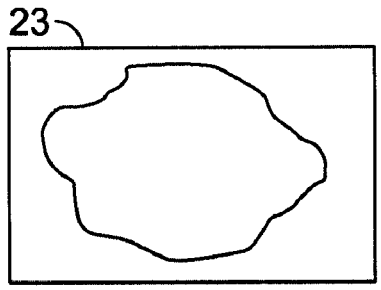
Figure 3B:
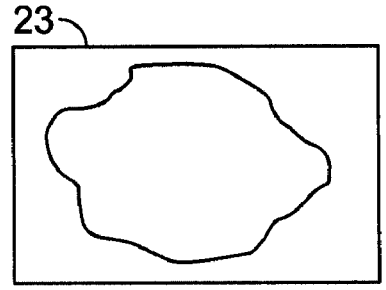
Figure 3C:
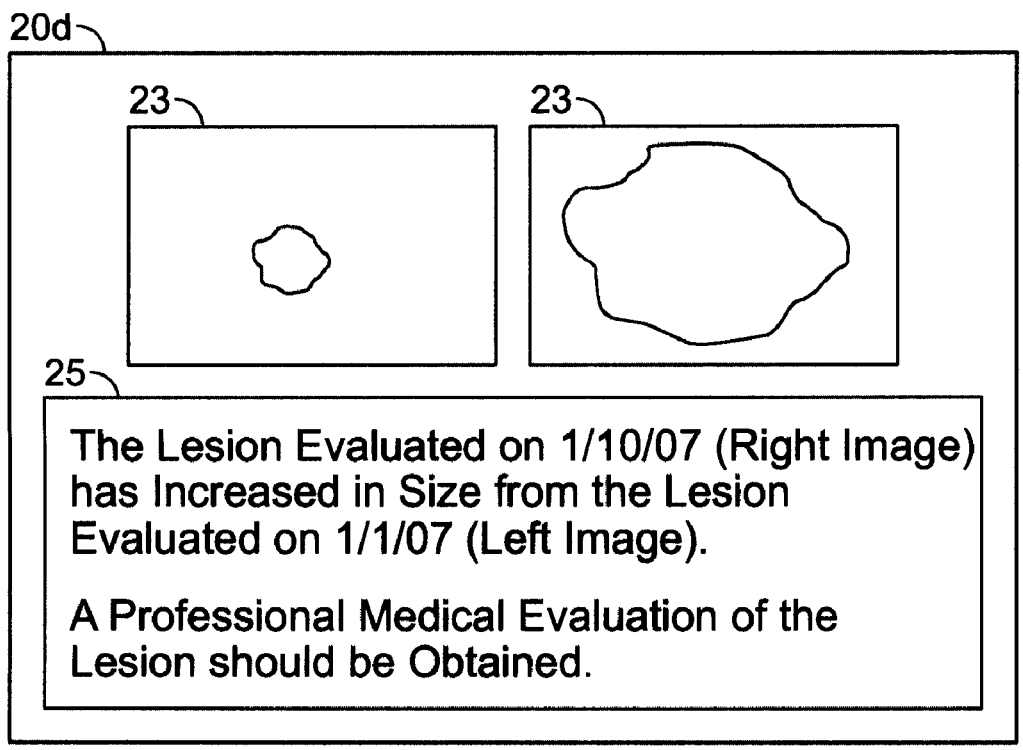
Figure 5:
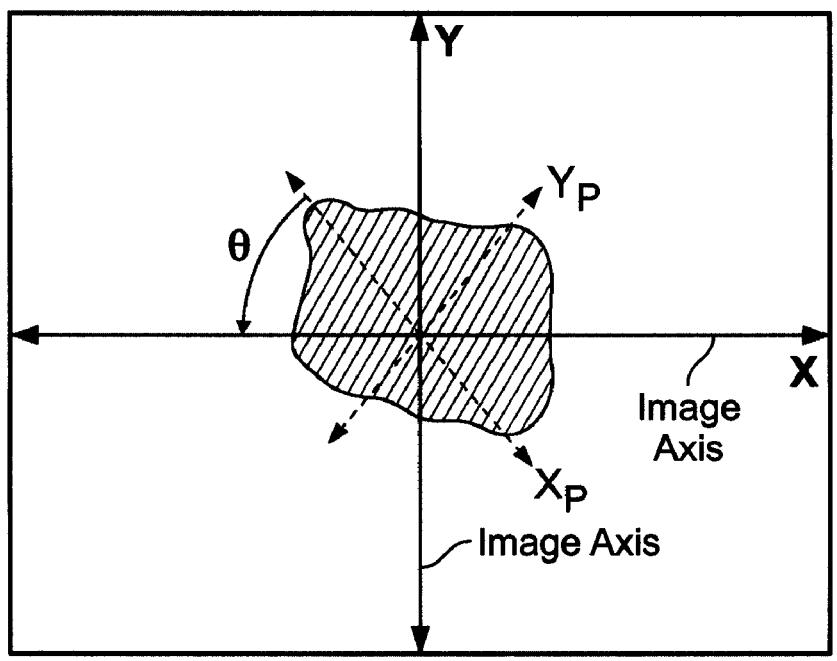
Figure 4:
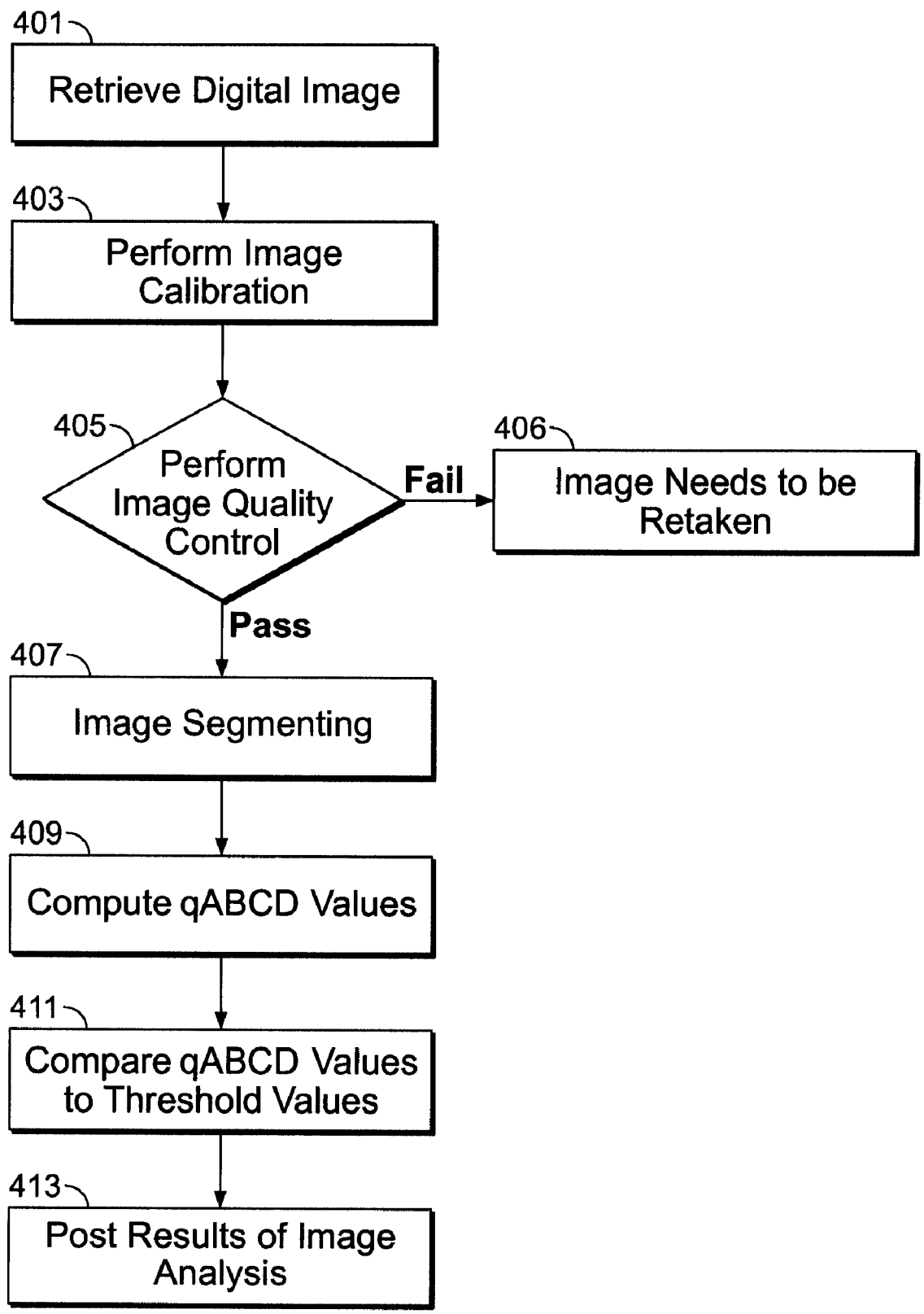

FIG. 1A is a block diagram.
FIG. 1B is a perspective view of an office.
FIG. 2 is a block diagram.
FIGS. 3A, 3B and 3C are screen shots.
FIG. 4 is a process diagram.
FIG. 5 is a diagram of a lesion.

An example of a way to analyze skin lesions or other skin conditions using a skin characteristics analysis device 2 (which, for this example, we sometimes call a lesion analysis device) is shown schematically in FIG. 1A. The steps of this analysis will be described generally, with reference to FIG. 1A, after which each step and the device will be described in further detail.

Traditionally, a person interested in knowing whether a skin lesion on his or her body is malignant will visit a medical professional who proceeds to examine the lesion. The medical professional will decide whether this lesion is in need of a biopsy to rule out malignancy. According to the present disclosure, however, that person may first obtain information which indicates whether an evaluation by the medical professional is necessary.

As shown in FIG. 1A, a user 4 interested in the condition of a skin lesion operates a lesion analysis device 2 to determine, for example, whether she/he should seek professional examination of the lesion. The device 2 can be used in a non-clinical setting, such as the user's home, a service center, or, alternatively, in a clinical setting, such as a physician's office. The user 4 can be a patient having the skin lesion or someone who is helping the patient, if the lesion is located on a region of the patient's body that is not easily accessible. It is not necessary for the user to be a physician. Furthermore, it is not necessary for the user 4 to have the lesion that is being analyzed on her/his skin.

In some implementations, the device 2 can be used by a primary care physician or other physician that does not specialize in dermatology. For example, FIG. 1B shows that a primary care physician 3 may provide the device 2 on a wall in her/his office not unlike an otoscope 5 and opthalmoscope 7. The primary care physician 3 may use the device 2 to perform a preliminary examination of one or more lesions during an annual patient physical. Should the device 2 indicate that a skin lesion requires further analysis, the physician 3 can advise a patient to have the lesion evaluated by a dermatologist or other physician specializing in the field of dermatology.

The user 4 applies the lesion analysis device 2 to a region of skin that includes the skin lesion and activates the device (101) to cause a digital image of the lesion to be obtained. The imaged lesion may either be pigmented or non-pigmented. The lesion analysis device 2 then performs a quantitative analysis (103) of the digital image to determine the presence or absence of one or more characteristics indicative of the lesion condition. As a result of the analysis, the device 2 provides information to the user (105) relating to the lesion condition. For example, the device 2 may notify the user 4 that the lesion is unlikely to be malignant or that the user should have the lesion further evaluated by a medical professional, such as a dermatologist. The information also can include a reminder that lesions with changing features should be seen by a medical professional regardless of the results provided by the device 2.

An example of the lesion analysis device 2 is shown in FIG. 2. The device includes a handheld RGB digital camera 10 having a memory 11 and a sensor, such as a CCD sensor, that acquires digital images in at least three channels: red 13, green 15, and blue 17. A separate attachment 12 to the digital camera includes an illuminator (14a and 14b), a polarizer 16 and a glass plate 18. The camera 10 may be connected to a desktop or laptop computer 20 having a digital input 20a, a memory 20b, a processor 20c and a display 20d. Software stored in the memory 20b instructs the processor to perform the quantitative analysis of the received images. Alternatively, the computer may be a handheld device, such as a personal digital assistant (PDA), which can be attached to the camera 10 using a wired or wireless connection. The use of handheld components allows the entire device 2 to be portable or stored inconspicuously in the user's home. Moreover, the camera 10, illuminator (14a, 14b), polarizer 16, glass plate 18, computer 20 and software functionality can be integrated in a single self-contained unit or PDA.

All the hardware components to the device, including the camera 10, attachment 12, and computer 20 can be off-the-shelf components, i.e., they are ready-made for a variety of uses and available for sale, lease, or license to the general public. Accordingly, an inexpensive lesion analysis device may be produced due to a reduction in assembly time and costs. Other implementations for acquiring and storing the images may be used as well. The lesion analysis device 2 may have access to other computers 24 or servers 26 through a network 22, such as the Internet. The device 2 may be connected to the network 22 by means of a variety of network connections such as a phone line, a cable or a wireless link.

FIG. 2 also shows a schematic illustration of a way to use the device 2 to analyze a region of skin that may include a skin lesion. The device 2 is positioned against the region of skin of interest such that the glass plate 18 is firmly in contact with the skin. For clarity, however, in FIG. 2, the plate is shown at a small distance from the surface of the skin. To initiate image acquisition, the user 4 first activates the device 2. The device may be activated, for example, by depressing a key on the computer 20 or pushing a button on the camera 4. Other methods of activating the device may be used as well. In response to activation of the device, the illuminator (14a, 14b)

illuminates (201) the region of skin with light. The light path is indicated by the arrows 201, 203 and 205 in FIG. 2. The illuminator (14a, 14b) can be any light source that provides broad band or white polarized light. Alternatively, the light provided by the illuminator can be polarized before reaching the glass plate 18. Examples of illuminators include white light emitting diodes and incandescent light, although other white light sources may be used as well.

The light travels through the glass plate 18, is reflected off the skin, travels back (203) through glass plate 18 and then passes (205) the polarizer 16 so that specular reflection is minimized. The polarized light then is acquired by the digital camera 10, which produces a digital image of the region of skin in at least three channels (R, G B). The digital image can be saved on the camera 10 or on the computer 20 for storage, viewing and processing. In either case, the digital image, or a copy of it, is passed from the camera 10 to the computer 20.

The computer 20 has a digital input 20a for receiving the digital images from the camera 10. The digital input 20a can include any conventional device that allows data to be transferred between the camera 10 and computer 20. For example, the digital input 20a may be a universal serial bus connection. Alternatively, the digital input 20a may be a wireless connection. Other types of digital inputs may be used as well. The memory 20b serves to store the digital images received from the camera 10 as well as software that is used to control the image analysis. Examples of memory 20b include the computer's hard drive, read only memory, random access memory, floppy disks, CD-ROM, or DVD-ROM. Other suitable media may be used as well.

The processor 20c, under the control of the software, performs image analysis on the received image and provides the results of the analysis to display 20d. Examples of the display 20d include cathode ray tube monitors, liquid crystal display monitors and touch-sensitive screens. Other displays may be used as well. Example screen shots of what a user would see on the display 20d are shown in FIGS. 3A-3C. The example screen shots include the imaged area of skin 23 with a pigmented skin lesion and a message 25 reporting the condition of the imaged lesion based on the quantitative analysis. If there is more than one lesion in the field-of-view of the camera, each lesion is analyzed separately, and the message 25 reports on all lesions separately. The received image and the results also may be transmitted over the network 22 to another computer automatically or in response to a user request. For example, if the device 2 indicates that a lesion is in need of further evaluation by a medical professional, the image data and quantitative analysis data may be automatically sent to a computer 24 in a physician's office specified by the user. Alternatively, the lesion condition may be announced by an audible tone or visible indicator (for example, a light emitting diode) in which one tone or color indicator is used to denote the lesion does not need further evaluation (e.g., is benign) and a different tone or color indicator is used to specify that the lesion is in need of further evaluation. The data obtained by the device may also be uploaded to a server 26 located locally or at some other remote site. Furthermore, if the device 2 is unable to identify the lesion as benign, it can automatically or, at a user's request, submit an electronic request to the physician's computer to schedule an appointment for evaluation of the lesion (see FIG. 3A).

Additional lesion information, which does not relate to screening for malignancy, may also be provided. For example, the device 2 may indicate the sub-classification to which a benign lesion likely belongs (such as seborrheic keratosis, melanocytic nevus, etc.). Furthermore, if a user is unsure whether a lesion is increasing in size or changing color, the device 2 may be used to store images at successive points in time to ascertain lesion characteristics over a period of time. The results of quantitative analysis for the different images may then be compared. If the analysis indicates that a lesion has changed, the device 2 notifies the user 4 and suggests further evaluation by a physician (see FIG. 3C).

In some implementations, the device 2 also may enable payments based on each instance the device is operated. For example, a user may enter a patient's account information into the device and, after a predetermined number of device operations (which include image acquisition and analysis), the account information may be transferred over the network to the server 26 where the charge for use is processed. Other ways of paying for utilizing the device 2 may be incorporated as well.

The steps carried out by the processor 20c to determine whether the region of skin contains a benign lesion or one that is in need of further evaluation can include (1) image calibration, (2) image quality control, (3) lesion segmentation and (4) lesion analysis, as discussed in the next section.

FIG. 4 shows a block diagram describing an example of how a lesion image is calibrated and segmented. In a first step, the digital image is retrieved (401) from the camera 10 or from memory 20b. Following image retrieval, spatial inhomogeneities introduced by the device are removed (403) in a calibration step. These inhomogeneities may be due to illumination non-uniformity, optical aberrations, variable quantum efficiency of the sensor elements and other non-uniformities in the device. To correct for these non-uniformities, the computer can perform a flat-fielding calibration. Flat-fielding calibration removes the non-uniformities by dividing, in each channel, each received image pixel-by-pixel by a white calibration image.

Flat-fielding also establishes a proper color balance for the system. The white calibration image may be obtained by imaging a white target of uniform reflectance in order to have a measure of the non-uniformities introduced by the device. The calibration image can be stored in the memory of the computer prior to first use so that the user is not required to obtain calibration images. The white calibration target may also be provided to the user for obtaining calibration images.

Once the received image has undergone calibration, the image is analyzed for quality (405) in an image quality control step. For example, the received image is checked for overexposure, underexposure, whether a lesion is present, whether the lesion is fully in the field-of-view of the camera, whether one or more dark spots are due to normal skin features or hair, and whether those spots can be easily removed through further image processing. Other checks for image quality may be implemented as well. If the processor 20c determines that the image fails the quality checks, the processor may display (406) a report to the screen indicating that the image needs to be re-taken. Alternatively, the processor may display a report that the image cannot be analyzed.

Following image quality analysis, the image is segmented (407) using segmentation algorithms. Examples of segmentation algorithms are described in U.S. Pat. No. 6,208,749, incorporated here in its entirety. In general, image segmentation entails separating the received image into regions that belong to a lesion and regions that are normal skin.

During lesion analysis, the software may instruct the processor 20c to analyze the lesion image based on a set of parameters corresponding to clinical characteristics. After performing the analysis, the processor may provide information to the user that is indicative of the lesion condition. For example, the processor 20c may determine that the lesion is benign or that there is insufficient data for a definitive medical diagnosis and subsequently post (413) the results of its calculation on the display 20*d*.

Examples of pigmented lesion characteristics useful in evaluating a lesion's condition include a set of four parameters known as ABCD characteristics. Traditionally, these four characteristics are determined visually and provide a subjective means for physicians and patients to identify pigmented skin lesions that could be melanoma. The four parameters represented by the ABCD characteristics are lesion asymmetry (A), border irregularity (B), color variegation (C) and lesion diameter (D).

Although the ABCD characteristics are typically assessed visually, it is also possible to define and quantify those characteristics so as to provide an objective means of analyzing pigmented skin lesions for melanoma. Quantitative ABCD characteristics (called qABCD) corresponding to the ABCD characteristics may be obtained by applying a set of mathematical algorithms to each segmented digital image that contains a lesion. In the general population, having at least one qABCD characteristic has a high sensitivity to melanoma and, at the same time, a high specificity, in which sensitivity is the probability that melanoma is classified correctly in a patient and specificity is the probability that a benign lesion is correctly classified in the patient.

Among lesions biopsied by a dermatologist, however, qABCD characteristics may not provide complete discrimination of melanomas from other pigmented skin lesions. Therefore, qABCD characteristics, alone, may not be sufficient for a medical diagnosis of melanoma, but remain useful as a first identification of pigmented skin lesions which require further evaluation.

Accordingly, in some implementations, the device 2 may be programmed to determine whether qABCD characteristics are present in an imaged pigmented lesion. The processor 20*c* computes (409) a value (called a qABCD value) for each qABCD characteristic from a corresponding mathematical algorithm. Each qABCD value is then compared (411) to a corresponding threshold value. If the qABCD value is above the threshold, a qABCD characteristic is determined to be present. If the qABCD value is below the threshold, the qABCD characteristic is determined to be absent. Should the processor 20*c* establish that a minimum of one qABCD characteristic is present in the imaged lesion, a report is provided to the display 20*d* indicating that professional medical evaluation of this lesion should be obtained. Alternatively, the minimum number of qABCD characteristics can be increased to two or more. If no qABCD characteristics exist, the processor 20*c* provides a report to the display 20*d* indicating that the lesion is unlikely to be melanoma. The reports also may be uploaded through the network to a physician's computer.

In some implementations, the reports provided by the computer 20 also may include a display of the imaged lesion in color or in different spectral bands. In some implementations, the reports may include the image analysis data provided by the mathematical algorithms as well as the threshold values. In addition, the reports may compare the image analysis results for two or more lesions. For example, images of lesions which have been analyzed over a period of time may be displayed in a side by side comparison along with the corresponding image analysis data.

As explained above, mathematical algorithms are applied to the digital image to obtain the qABCD value for each qABCD characteristic. A discussion of examples of such algorithms may be found in U.S. Pat. No. 6,208,749. The lesion asymmetry (A) algorithm provides a measure of the geometric asymmetry of the lesion. To determine this value, a binary mask generated from the lesion image is used to evaluate the lesion orientation. Typically, the mask is generated during the image segmentation step (407) and stored in memory for later use.

If imaged lesions are to be compared over time or with other lesions, the lesion asymmetry value should be independent of the lesion orientation in the image. Therefore, the binary mask image is rotated by a lesion orientation angle $\theta$ to align the lesion principal axes ($x_p$, $y_p$) with the image axes (see FIG. 5). The angle $\theta$ is computed based on the lesion mask. For symmetric lesions, the principal axes are the symmetry axes. Once the mask has been rotated, the lesion asymmetry can be determined with respect to the principal axes. For each principal axis, the fraction of the lesion pixels which do not have a counterpart on the opposite side of the principal axis is determined. The asymmetry value is the sum of these fractions for two principal axes and thus is a measure of asymmetry in the geometric shape of a lesion. Other measures of asymmetry could also be used.

The border irregularity (B) algorithm is often defined as a ratio of a measured lesion perimeter to the perimeter of a circle having the same area as the lesion. However, because the perimeter is difficult to estimate reproducibly, a statistical descriptor of border irregularity may be used. In addition, many lesions are elongated and an ellipse may be a better approximation for the shape of the comparison lesion than a circle.

If a statistical descriptor is to be used for an elongated lesion, one first determines a lesion intensity centroid, an orientation angle, and an aspect ratio using the binary lesion mask. The aspect ratio is defined as $$AR = \frac{\sqrt{\langle x' - x_c \rangle^2}}{\sqrt{\langle y' - y_c \rangle^2}} \qquad (1)$$

where the prime refers to the coordinate system defined by the lesion principal axes and the subscript c represents the lesion intensity centroid. In addition, the angular brackets denote the moment of intensity.

These values may then be used to construct an ellipse that is the best regular approximation of the lesion border. For each lesion border pixel, the angle between a line connecting this pixel to the lesion centroid and the horizontal axis is determined. A location on the ellipse border is determined for the same angle and a distribution of the distances between the ellipse border and the lesion border is computed. The border irregularity value may then be defined as the ratio of the standard deviation to the mean value of this distribution.

The color variegation (C) algorithm is defined as the ratio of the standard deviation of reflectance to the average reflectance over all of the pixels of the lesion in the spectral band centered at 700 nm. A wavelength of 700 nm is used because the pixel-to-pixel variability of lesion reflectance has been shown to have a maximum in the red spectral band, i.e., for wavelengths between 650 and 700 nm. However, since the spectral band of the red sensor or filter may not be centered at 700 nm, other wavelengths may be used as well.

The lesion dimension (D) algorithm is defined as the maximum distance (in millimeters) between two pixels on a lesion border instead of the lesion diameter because lesions are rarely circular.

Each of the qABCD values obtained using the above algorithms on an imaged pigmented lesion is evaluated against a corresponding threshold value to determine whether or not a qABCD characteristic is present. The threshold values may be pre-calculated for the specific imaging system and stored on the device 2 before first use. A pre-calculated threshold value is calculated as the qABCD value which maximizes a diagnostic accuracy of a corresponding qABCD characteristic in a sample database containing previously imaged and biopsied pigmented skin lesions. The sample database of biopsied lesions includes both clinically evaluated malignant melanomas and benign lesions. The diagnostic accuracy may be defined as DA=TP/(TP+FN+FP) where TP is the number of true positives (correctly identified melanoma in the sample database), FN is the number of false negatives (malignant lesions incorrectly identified as benign in the sample database) and FP is the number of false positives (benign lesions incorrectly identified as malignant in the database). However, different imaging devices may have different spatial resolutions, different illuminators that provide varying spectra of light, different sensor efficiencies, and different thermal noise. Therefore, the same threshold values may not be used for all imaging devices and may need to be determined independently for each imaging system. In addition, updated threshold values may be obtained by downloading them over the network connection from a server or other computer.

Clinical lesion characteristics other than qABCD can be evaluated by the device 2, as well. For example, an alternative set of lesion characteristics known as qRING characteristics may be evaluated in a similar manner to the qABCD characteristics. The RING acronym stands for the following parameters: mean lesion reflectance (R); lesion inhomogeneity measured by blotchiness (I); lesion network irregularity measured by irregularity of rete ridges (N), in which a rete ridge is an epidermal thickening that extends downward between dermal papillae; and gradient of the lesion border (G). The value for the mean lesion reflectance is determined using a digital image recorded in a red spectral band. The values for lesion inhomogeneity, network irregularity and border gradient are determined using digital images recorded in a blue spectral band. Digital images in both red and blue spectral bands may be obtained from the red and blue channels of the sensor in the camera 10. Similar to qABCD, quantitative RING (qRING) characteristics may be verified by comparing qRING values to corresponding threshold values, in which the threshold values are pre-calculated using a sample database. If one or more qRING characteristics are determined to be present in the lesion image, a report may be provided to the display 20d indicating that professional medical evaluation should be obtained. Other lesion characteristics may analyzed as well.

Although the qRING characteristics do not correspond directly to visible characteristics that professionals have traditionally used to evaluate skin lesions, the qRING characteristics provide as good sensitivity and better specificity than qABCD for lesions that have been clinically evaluated.

Although the characteristics specified above are used to identify possible melanoma, the device 2 can also identify other pigmented and non-pigmented skin lesions that should be evaluated by a physician including, for example, actinic keratosis, psoriasis, basal cell carcinomas, and squamous cell carcinomas.

Certain implementations may have one or more of the following advantages. The lesion analysis device objectively and automatically determines lesion characteristics and makes straightforward comparisons to clinical evaluations of the characteristics. Furthermore, the lesion analysis device can be used as an objective tool for lesion identification. In addition, the device can provide a preliminary analysis of pigmented skin lesions without requiring evaluation by a dermatologist or other physician.

Other implementations and features are within the scope of the following claims.

For example, other conditions of interest of a person's skin may be imaged and the images analyzed quantitatively to determine whether additional analysis of an expert would be desirable. Such conditions include other health related conditions of the skin as well as other conditions of the skin that are not health related, for example, cosmetic conditions related to aging or beauty. Any condition on the surface or inside the skin that is of interest could be subject to such analysis. In each case, statistical data about the general population could be used as the basis to make a quantitative determination that is not necessarily accurate enough to be definitive but is accurate enough to suggest the need for an expert review. For example, a user could be advised whether a health-related or cosmetic skin condition would be susceptible to treatment by any chemical composition or whether further evaluation by an expert would be useful to make a final determination of that question.

Although in the examples given in the discussion above, the device is shown as a camera, an illuminator, and a computer, a wide variety of other implementations that use commercially available equipment may be possible now and in the future. It may be possible to do the processing directly in the digital camera and to display the result on the screen of the camera. The illuminator may be unnecessary in certain circumstances. The computer could be replaced by a variety of handheld devices. Eventually, it may be possible to use the digital camera and on-board processing capability of a cellular telephone to perform the entire process and display the result on the screen of the telephone.

In some implementations, the device may display an image of a body-map on which a user can identify a region that has been analyzed or a region that will be analyzed by the device. Moreover, a touch-sensitive display may allow a user to select the lesion location on the body-map image.

Although some of the examples discussed earlier refer to the use of the device either by a person in the general population or by a physician, including a dermatologist or a non-dermatologist, the user could have any of a wide variety of other roles, including, a nurse, a paramedical, a health care worker, a retail store clerk, a cosmetologist, a caregiver, a trainer, a coach, a pharmacist, a family member, or a friend, to name a few.

In addition, the knowledgeable person could be other than a dermatologist, for example, a non-dermatologist physician, a health care worker, or a cosmetologist, to name a few.

The person whose skin is being analyzed need not be a patient, as suggested in some of the implementations described earlier, but could be any person having any role in the general population, including an athlete, a performer, a teenager, a consumer, or a traveler, to name a few.

The contexts in which the analysis could be performed need not be limited to the locations previously named, but could include any place where it is convenient or desirable to do so, including, for example, an examination room, an outpatient clinic, a pharmacist's facility, a waiting room, an airport, a retail store, a school, a nurse's office, a place of employment, a cruise ship, a beach cabana, or a resort facility, to name a few.

The analysis device can be implemented in a wide variety of form factors, including hand held devices, desktop devices, devices installed in buildings, rooms, vehicles, and any other place where such an analysis would be desirable or convenient.

The specificity and sensitivity levels of the analysis can vary over a range and still provide useful information to the user.

A variety of quantitative analyses can be used to obtain the information to be provided to the user.

The population to which the classification applies need not be the general population, but could be for example, a population limited by various demographic characteristics, such as ethnic background, skin color, geography, sex, or age.

The parameters used in the analysis can all be ones that correspond to visible familiar skin characteristics, can all be ones that do not correspond to any familiar visible skin characteristics, or can be a mixture of the two.

A wide variety of display and audio techniques can be used to indicate to the user the result of the quantitative analysis.

What is claimed is:

1. An apparatus comprising:
a device to acquire a digital image of an area of skin, and
a processor to
quantitatively analyze the digital image to determine a characteristic of all or part of the area of skin that is indicative of a skin condition of interest, and
depending on a result of the quantitative analysis, provide information to a user about the area of skin relative to the condition of interest, the information comprising an indication to the user whether a knowledgeable person should evaluate the area of skin.

2. The apparatus of claim 1 in which the quantitative analysis includes comparing the characteristic of all or part of the area of skin to a threshold associated with the condition of interest.

3. The apparatus of claim 1 in which part of the area of skin comprises a pigmented lesion.

4. The apparatus of claim 1 in which the condition of interest comprises malignancy.

5. The apparatus of claim 1 in which the quantitative analysis suggests that malignancy cannot be ruled out.

6. The apparatus of claim 5 in which the processor provides an indication to the user of the advisability of having the area of skin evaluated by a physician.

7. The apparatus of claim 1 in which the quantitative analysis suggests that malignancy can be ruled out.

8. The apparatus of claim 7 in which the processor provides an indication that it is not necessary to have the area of skin evaluated by a knowledgeable person.

9. The apparatus of claim 1, 6 or 8 in which the knowledgeable person is a physician and the user is not a physician.

10. The apparatus of claim 1, 6 or 8 in which the knowledgeable person is a dermatologist and the user is a physician other than a dermatologist.

11. The apparatus of claim 1 in which the user is not a licensed health care provider.

12. The apparatus of claim 1 in which the device acquires different digital images of the area of skin at different times and the processor quantitatively analyzes each of the different digital images.

13. The apparatus of claim 12 in which the processor compares the results of the quantitative analysis for each image and, based on the comparison, indicates whether a change in a condition of the area of skin has occurred.

14. The apparatus of claim 1 also comprising an audible or visible indicator to provide the indication.

15. The apparatus of claim 1 in which the device to acquire the digital image is configured to be applied to the skin.

16. The apparatus of claim 1 in which the device is triggered by the user to acquire the digital image.

17. The apparatus of claim 1 in which at least part of the apparatus is handheld.

18. The apparatus of claim 1 in which the information provided to the user comprises a classification of the skin condition of interest.

19. The apparatus of claim 1 in which the characteristic that is indicative of a skin condition of interest has a high specificity and high sensitivity.

20. The apparatus of claim 19 in which both the specificity and sensitivity are greater than 90 percent in the general population.

21. The apparatus of claim 1 in which the characteristic that is indicative of a skin condition of interest is not recognizable by visual inspection by a physician.

22. A method comprising:
a processor:
performing quantitative analysis on an image of an area of skin to determine a characteristic of all or part of the area of skin that is indicative of a condition of interest; and
providing information to a user, based on the quantitative analysis, about the area of skin relative to the condition of interest, the information comprising an indication to the user whether a knowledgeable person should evaluate the area of skin.

23. The method of claim 22 comprising:
acquiring images of the area of skin at different times;
performing quantitative analysis on each of the images to determine, for each image, a characteristic of all or part of the area of skin;
comparing the results of the quantitative analysis for each image; and
providing information to the user, based on the comparison, that indicates whether a change in a condition of the area of skin has occurred.

24. The method of claim 22 in which the knowledgeable person is a physician and the user is not a physician.

25. The method of claim 22 in which the knowledgeable person is a dermatologist and the user is a physician other than a dermatologist.

26. A method comprising:
a processor that quantitatively determines, based on an image of a person's skin and on statistical information about skin of people in a general population, whether the person's skin is or is not characterized by a condition of interest, in which the quality of the determination is sufficient to reliably indicate whether examination of the skin relative to the condition of interest by an expert is desirable.

27. A method comprising:
a processor that automatically analyzes an image of a region of skin of a person, and
automatically provides an indication that a condition of the region of skin should be analyzed further by a human expert.

28. A method comprising:
a processor that quantitatively determines values of qABCD parameters from images of skin lesions;
and determines, based on statistical information from a general population, with a high sensitivity and specificity between lesions that are non-melanoma and lesions that cannot be ruled out as melanoma; and
and provides an indication of the result of the determination that is based on statistical information.

29. The method of claim 28 comprising:
comparing each qABCD parameter value to a corresponding threshold value;

determining that a qABCD characteristic is present if a corresponding qABCD parameter value is greater than the corresponding threshold value; and determining that qABCD characteristics are absent if each qABCD parameter value is less than the corresponding threshold value.

30. The method of claim 29 comprising deriving each threshold value from a reference database of imaged skin lesions wherein each threshold value maximizes a diagnostic accuracy of a corresponding qABCD parameter value.

31. The method of claim 29 comprising:

providing an indication of the advisability of having one or more of the skin lesions evaluated by a knowledgeable person if a qABCD characteristic is present in the one or more skin lesions.

32. The method of claim 28 in which the sensitivity and specificity are greater than 90 percent.

33. A method comprising:

a processor that quantitatively determines values of qRING parameters of images of skin lesions;

and determines, based on statistical information from a general population, with a high sensitivity and specificity between lesions that are non-melanoma and lesions that cannot be ruled out as melanoma; and and provides an indication of the result of the determination that is based on statistical information.

34. The method of claim 33 comprising:

comparing each qRING parameter value to a corresponding threshold value;

determining that a qRING characteristic is present if a corresponding qRING parameter value is greater than the corresponding threshold value; and determining that qRING characteristics are absent if each qRING parameter value is less than the corresponding threshold value.

35. The method of claim 34 comprising deriving each threshold value from a reference database of imaged skin lesions wherein each threshold value maximizes a diagnostic accuracy of a corresponding qRING parameter value.

36. The method of claim 34 comprising:

providing an indication of the advisability of having the skin lesions evaluated by a knowledgeable person if one or more qRING characteristics is present.

37. The method of claim 33 in which the specificity and sensitivity are greater than 90 percent.

38. An apparatus comprising:

a camera for acquiring a digital image of a region of skin that includes a skin lesion;

a processor connected to the camera, in which the processor is programmed to:

quantitatively analyze the digital image to determine the presence of a characteristic, indicative of malignancy, in the skin lesion, provide an indication to a user to have a knowledgeable person evaluate the skin lesion if the characteristic is present; and provide an indication to the user that it is not necessary to have the skin lesion evaluated by a knowledgeable person if the characteristic is not present; and a display for viewing the skin lesion image and indication provided by the processor.

39. The apparatus of claim 1 in which the information is not necessarily sufficient for a definitive medical diagnosis.

40. The method of claim 22 in which the information is not necessarily sufficient for a definitive medical diagnosis.

* * * * *